United States Patent
Chen

(10) Patent No.: US 6,818,769 B2
(45) Date of Patent: Nov. 16, 2004

(54) PROCESS FOR THE PREPARATION OF DIAMINE SINGLE-SIDED CONDENSATION PRODUCTS

(75) Inventor: Bor-Kuan Chen, 1582 Jackson St., Santa Clara, CA (US) 95050

(73) Assignee: Bor-Kuan Chen, Santa Clara, CA (US)

( * ) Notice: Subject to any disclaimer, the term of this patent is extended or adjusted under 35 U.S.C. 154(b) by 60 days.

(21) Appl. No.: 10/418,716

(22) Filed: Apr. 17, 2003

(65) Prior Publication Data

US 2004/0210054 A1 Oct. 21, 2004

(51) Int. Cl.$^7$ .............................................. C07D 401/04
(52) U.S. Cl. ..................... 544/331; 544/333; 546/274.1
(58) Field of Search .................................. 544/333, 331, 544/330, 332, 334, 335; 546/274.1

(56) References Cited

U.S. PATENT DOCUMENTS

| | | | |
|---|---|---|---|
| 4,742,060 A | 5/1988 | Shiokawa et al. | 514/252 |
| 6,307,053 B1 | 10/2001 | Yeh et al. | 546/274.7 |
| 6,465,492 B1 | 10/2002 | Yeh et al. | 514/340 |

*Primary Examiner*—Richard L. Raymond

(57) ABSTRACT

Disclosed is a preferred process for preparation of heterocyclic diamine single-sided condensation products. The process involves gradually co-feeding stoichiometric amounts of a pyridyl compound and a heterocyclic diamine compound into an organic solvent in the presence of an alkali carbonate while heating at $\geq 60°$ C. This process can increase the reaction rate, improve yield, minimize double-sided condensation byproduct, and produce a high-quality product.

5 Claims, No Drawings

PROCESS FOR THE PREPARATION OF DIAMINE SINGLE-SIDED CONDENSATION PRODUCTS

BACKGROUND OF INVENTION

This invention relates to a novel process for the preparation of heterocyclic diamine single-sided condensation products by condensating a pyridyl compound with a heterocyclic diamine compound. For example, condensating 2-chloro-5-chloromethyl pyridine with 2-nitroimino imidazolidine to form the corresponding compound, imidacloprid.

U.S. Pat. Nos. 4,742,060 and 6,465,492 disclose heterocyclic diamine compounds with the formula (I)

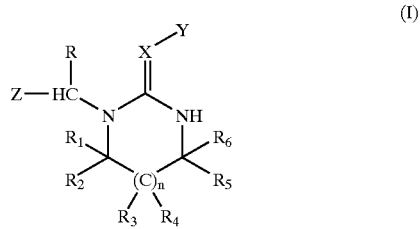

wherein n=0 or 1; X=N or C—$R_7$, $R_7$ is hydrogen; Y=$NO_2$ or $SO_2R_8$, $R_8$ is hydrogen, a $C_1$–$C_4$ alkyl group, a $C_1$–$C_4$ alkoxy group, a $C_2$–$C_4$ alkenyl group, or an aryl group; Z=pyridyl group optionally substituted by a halogen atom; R=hydrogen or methyl group; $R_1$ to $R_8$=hydrogen.

The above heterocyclic diamine compounds are useful as pesticides. At present, the most widely used compound is imidacloprid, a neonicotinoid insecticide. These compounds can be synthesized by reacting a pyridyl compound with a heterocyclic diamine compound in the presence of an alkali base in an organic solvent. The alkaline base can be NaH or an alkali carbonate. However, NaH is preferred over alkali carbonate for this single-sided condensation reaction because it produces a better yield. When alkali carbonate is used in the aforementioned condensation reaction, a relatively large amount of byproduct is produced. This condensation reaction can be represented as follows:

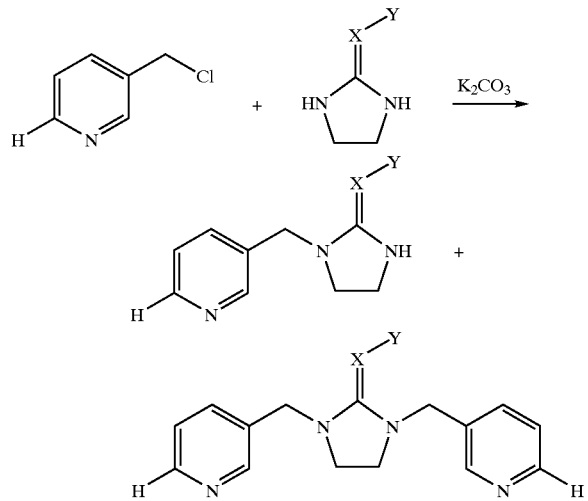

wherein H is a halogen atom, e.g. chlorine.

However, using NaH increases cost and gives rise to safety hazards and transportation problems. Due to these drawbacks, a two-step reaction process had been proposed: react a pyridyl compound with ethylenediamine to form an intermediate that is treated with S-methyl-N-nitroisothiourea to afford a single-sided condensation product. Although this method overcomes the safety concerns and transportation problems from using NaH, the two-step reaction process is complicated, costly, and unpractical.

U.S. Pat. No. 6,307,053 discloses another process for preparing imidacloprid. A stoichiometric amount of 2-chloro-5-chloromethyl pyridine is gradually added into a mixture of a corresponding stoichiometric amount of 2-nitroiminoimidazolidine and the organic solvent in the presence of an alkali carbonate under reflux condition. The yield of 90% imidacloprid from 2-chloro-5-chloromethyl pyridine is 90~92%. i.e. active yield is 81–83%. However, the purity of imidacloprid thus obtained is less than 95%, as required by the specification. Therefore, imidacloprid needs further purification before use.

BRIEF SUMMARY OF THE INVENTION

This invention provides a process for preparing heterocyclic diamine single-sided condensation products to overcome the aforesaid disadvantages. This preferred process can improve yield, minimize double-sided condensation byproduct, and produce high-quality product.

The process comprises of gradually co-feeding stoichiometric amounts of a pyridyl compound and a heterocyclic diamine compound simultaneously into an organic solvent in the presence of an alkali carbonate while heating. Due increased reactant concentrations, the molecular collision probability increases, which improves mass transfer, increases reaction rate, and minimizes byproduct formation.

DETAILED DESCRIPTION OF THE INVENTION

The novel preparation of heterocyclic diamine single-sided condensation products [chemical formula as shown in (I)] is described in detail as follows:

Separately dissolve a stoichiometric amount of pyridyl compound and an equivalent of a heterocyclic diamine compound in an organic solvent. Charge a minimum amount of organic solvent, a small amount of heterocyclic diamine compound, and an alkali carbonate in a reactor, then heat to $\geq 60°$ C. or reflux. Gradually co-feed the pyridyl solution and heterocyclic diamine solution into the organic solution while heating. After addition, hold the reaction for a short period of time to complete the condensation reaction.

Co-feeding is one of the key points of this invention. This novel approach of feeding reactants can increase reactant concentrations and molecular collision probability, which improves mass transfer, increases the reaction rate, and minimizes double-sided condensation byproduct formation. Metering pumps were utilized to control the feeding rate. The optimal feeding time is 4~6 hours. Less time caused lower yield and lower product purity. Feeding for longer than six hours is not economical. The total stoichiometric amount of heterocyclic diamine compound used is slightly greater than that of the pyridyl compound. The reaction uses 1.01~1.2 mol equivalent of the heterocyclic diamine compound. More preferred ratio is 1.05~1.10. This slight excess of heterocyclic diamine added to the initial solvent inside the reactor ensures product quality and avoids raw material waste. The organic solvent is selected from the group consisting of acetonitrile, ketones, alcohols, and DMF. Acetonitrile or methyl ethyl ketone is used. The alkali carbonate is either sodium carbonate or potassium carbonate. Potassium carbonate is selected. One to three equivalents of potassium carbonate are used, with an optimum amount of 1.5 equivalent.

Typical embodiment of the invention is described in detail for the preparation of imidacloprid. Equal mol of 2-chloro-5chloromethyl pyridine and 2-nitroiminoimidazolidine are separately dissolved in an organic solvent (e.g. acetonitrile). In a reactor, charge a minimum amount of organic solvent, 0.05~0.10 equivalent of 2-nitroiminoimidazolidine, and 1.5 equivalents of potassium carbonate, then heat to $\geq 60°$ C. Gradually, the 2-chloro-5-chloromethyl pyridine solution and 2-nitroiminoimidazolidine slurry are co-fed into the prepared organic solution at $\geq 60°$ C. for a period of 4~6 hours. Hold the temperature for an additional period of time to complete the condensation reaction.

For the purposes of promoting a further understanding of the invention, its preferred features and advantages, the following specific example and comparative example are provided. It should be understood that these examples are illustrative and do not limit the invention.

EXAMPLE

In a 2-liters glass reactor equipped with a mechanical stirrer, condenser, feed lines, and thermometer. 3.25 g (0.025 mol) of 2-nitroiminoimidazolidine and 104 g (0.75 mol) of potassium carbonate were dissolved in 100 ml of acetonitrile. These compounds were mixed completely and heated to reflux. In separate reactors, 81 g (0.5 mol) of 2-chloro-5-chloromethyl pyridine was dissolved in 300 ml of acetonitrile, and 65 g (0.5 mol) of 2-nitroiminoimidazolidine was mixed with 400 ml of acetonitrile. Both the solution and slurry were continuously co-fed dropwise into the organic solution at reflux (83~84° C.) for a period of 4~5 hours. After completion of the condensation reaction, the mixture was subjected to hot filtration to remove salts and impurities. Then, the filtrate was further cooled to below 0° C., imidacloprid was precipitated out, washed with water, and 105 g was obtained with purity of 98.1%. The active yield was 80.6%. The filtrate was further concentrated under vacuum to recover acetonitrile for reuse. The residue was washed with methanol to remove residual impurities. An additional 18 g imidacloprid was recovered with a purity of 90.2%, i.e. yield of 12.7%. The total active yield based on 2-chloro-5-chloromethyl pyridine was 93.3%.

Comparative Example 7.8 g (60 mmol) of 2-nitroiminoimidazolidine and 12.1 g (87.5 mmol) of potassium carbonate were dissolved in 60 ml of acetonitrile in a reflux flask. The mixture was heated to a temperature sufficient for achieving reflux operating condition. 8.1 g (50.0 mmol) of 2-chloro-5-chloromethyl pyridine was dissolved in 40 ml of acetonitrile, and was dropwisely and continuously added into the flask under the reflux condition for a period of 5 hr, i.e., the addition rate was about 1.5 ml/minute. After completion of the reaction, the mixture was subjected to filtration. The filtrate was concentrated, and was further purified. The yield was 92.16% and the value of active ingredient (purity) was 90.6% (as determined by HPLC). The active yield was 83.5% (92.16%*90.6%).

I claim:

1. A process for preparation of heterocyclic diamine single-sided condensation products, chemical formula as shown in (I),

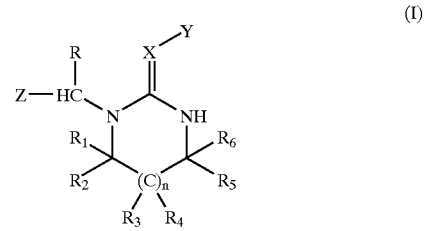

wherein n=0 or 1; X=N or C—$R_7$, $R_7$ is hydrogen; Y=$NO_2$ or $SO_2R_8$, $R_8$ is hydrogen, a $C_1$–$C_4$ alkyl group, a $C_1$–$C_4$ alkoxy group, a $C_2$–$C_4$ alkenyl group, or an aryl group; Z=pyridyl group optionally substituted by a halogen atom; R=hydrogen or methyl group; $R_1$ to R6=hydrogen, comprising:

(i) separately dissolve a stoichiometric amount of a pyridyl compound and an equivalent of a heterocyclic diamine compound in an organic solvent;

(ii) charge a minimum amount of organic solvent, small amount of heterocyclic diamine compound, and an alkali carbonate in a reactor, then heat to $\geq 60°$ C. or reflux;

(iii) gradually co-feed the pyridyl solution and heterocyclic diamine solution into the organic solution while heating, then hold the reaction for a short period of time to complete the condensation reaction.

2. The process of claim 1 wherein equal stoichiometric amounts of a pyridyl compound and a heterocyclic diamine compound are gradually and continuously co-fed (in 4~6 hours) into the organic solution while heating at $\geq 60°$ C.

3. The process of claim 1 wherein the total stoichiometric amount of heterocyclic diamine compound used is 1.01~1.2 mol equivalent to that of the pyridyl compound.

4. The process of claim 1 wherein the organic solvent is selected from acetonitrile or methyl ethyl ketone.

5. The process of claim 1 wherein the alkali carbonate is potassium carbonate, with use of one to three equivalents of potassium carbonate.

* * * * *